US009278072B2

(12) United States Patent
Klose et al.

(10) Patent No.: US 9,278,072 B2
(45) Date of Patent: Mar. 8, 2016

(54) HORMONAL CONTRACEPTIVE CONTAINING A COMBINATION OF ETHINYLOESTRADIOL AND CHLORMADINONE ACETATE

(75) Inventors: Janine Klose, Würselen (DE); Johannes Bartholomäus, Aachen (DE); Klaus-Michael Wilsmann, Roetgen (DE); Georg Schramm, Stolberg (DE)

(73) Assignee: Richter Gedeon Nyrt., Budapest (HU)

( * ) Notice: Subject to any disclaimer, the term of this patent is extended or adjusted under 35 U.S.C. 154(b) by 930 days.

(21) Appl. No.: 11/009,938

(22) Filed: Dec. 10, 2004

(65) Prior Publication Data

US 2005/0267084 A1   Dec. 1, 2005

(30) Foreign Application Priority Data

May 28, 2004   (DE) .......................... 10 2004 026 670

(51) Int. Cl.
| | | |
|---|---|---|
| *A61K 31/56* | (2006.01) |
| *A61K 9/28* | (2006.01) |
| *A61K 31/565* | (2006.01) |
| *A61K 31/57* | (2006.01) |
| *A61K 31/567* | (2006.01) |

(52) U.S. Cl.
CPC ............. *A61K 9/2866* (2013.01); *A61K 31/565* (2013.01); *A61K 31/567* (2013.01); *A61K 31/57* (2013.01)

(58) Field of Classification Search
USPC ...................................................... 514/170
See application file for complete search history.

(56) References Cited

U.S. PATENT DOCUMENTS

| | | | |
|---|---|---|---|
| 6,190,693 B1 | 2/2001 | Kafrissen et al. | |
| 6,265,393 B1 | 7/2001 | Heinrichs | 514/178 |
| 6,312,722 B1 | 11/2001 | Schmidt-Gollwitzer et al. | |
| 6,451,779 B1 | 9/2002 | Hesch | 514/171 |
| 6,500,814 B1 | 12/2002 | Hesch | |
| 6,511,970 B1 | 1/2003 | Rodriguez | |
| 2002/0061875 A1 | 5/2002 | Gast | |
| 2004/0063721 A1 | 4/2004 | Deecher | |
| 2004/0219174 A1* | 11/2004 | Kulmann | 424/400 |

FOREIGN PATENT DOCUMENTS

| | | |
|---|---|---|
| DE | 41 04 385 C1 | 2/1991 |
| DE | 42 24 534 A1 | 7/1992 |
| DE | 43 08 406 C1 | 3/1993 |
| DE | 43 39 934 A1 | 11/1994 |
| DE | 43 21 957 A1 | 1/1995 |
| DE | DE 43 21 957 C2 | 9/1995 |
| DE | 195 39 233 A1 | 4/1997 |
| DE | 34 86 422 T2 | 6/1997 |
| DE | 197 05 229 C2 | 4/1999 |
| DE | 197 39 916 C2 | 9/2001 |
| DE | 698 04 918 T2 | 11/2002 |
| DE | 601 01 276 T2 | 4/2004 |
| EP | 0 398 460 B1 | 5/1990 |
| EP | 0 398 460 A2 | 11/1990 |
| EP | 0 398 460 A3 | 11/1990 |
| EP | 0 253 607 A1 | 1/1998 |
| EP | 0 735 883 B1 | 11/2006 |
| WO | WO 86/01402 | 3/1986 |
| WO | WO 99/53910 | 10/1999 |
| WO | WO 02/094276 A1 | 11/2002 |
| WO | WO 2004/098517 A2 | 11/2004 |

OTHER PUBLICATIONS

"Progestogens with Antiandrogenic Properties", Daniel Raudrant, et al., Drugs 2003; 63 (5); 463-492.
"Rote Liste 2002", Rote Liste Service, 2002, Editio Cantor Verlag, Aulendorf, XP002339882.
"Orale Kontrazeptiva—Folge 1: Typen and Indikationen", B. Wetzka, et al., MMW-Fortschr. Med. 2001, pp. 40-42.
"Properties of Reactively Evaporated Gallium Oxide Thin Films", Mar. 1979, XP-000905106, pp. 13-17.
"Neues in der Gynakologischen Endokrinologie and Fortpflanzungsmedizin", T. Rabe, XP-002349009, Gynakologe 2002—35:845-860.
Acne Resolution Rates: Results of a Single-Blind, Randomized, Controlled, Parallel Phase III Trial with EE/CMA (Belara®) and EE/LNG (Microgynon®), I. Worret, et al., Pharmacology and Treatment, Dermatology 2001; 203:38-44.
"Etude portant sur une therapeutique sequentielle notamment dans les syndromes premenopausiques et menopausiques", P. Delacroix, Actualite Therapeutique, XP009055146, pp. 559-564.
"Chlormadinone acetate versus micronized progesterone in the sequential combined hormone replacement therapy of the menopause", C. Pelissier, et al., XP-002349010, Maturitas 40 (2001) 85-94.
Non Final Office Action issued on Mar. 12, 2009 by Examiner for corresponding pending U.S. Appl. No. 11/009,361.
Non Final Office Action issued on Apr. 16, 2009 by Examiner for corresponding pending U.S. Appl. No. 11/348,545.
Non Final Office Action issued on Sep. 2, 2009 by Examiner for corresponding pending U.S. Appl. No. 11/009,362.
G. Schramm, Contraceptive Efficacy and Tolerability of Chlormadinone Acetate 2mg/Ethinylestradiol 0.03mg (Belara®), Clinical Drug Invest 2002:22 (4) pp. 221-231.
Schramm et al.: "Contraceptive Efficacy and Tolerability of Chlormadinone Acetate 2mg/Ethinylestradiol 0.03mg (Belara) Results of a Post-Marketing Surveillance Study"; Clin Drug Invest, 2002, vol. 22(4), pp. 221-231.
Kuhl: "Aktuelle Entwick-lungen in der hormonalen Kontrazeption", Gynaekologe, 1992, vol. 25, pp. 231-240.
"Effect of 21-day and 24-day oral contraceptive regimens containing gestodene (60 μg) and ethinyl estradiol (15 μg) on ovarian activity", Helen Sullivan et al., Fertility and Sterility, vol. 72, No. 1, Jul. 1999, 115-120.
"The safety and contraceptive efficacy of a 24-day low-dose oral contraceptive regimen containing gestodene 60 μg and ethinylestradiol 15 μg", Gestodene Study Group 322, The European Journal of Contraception and Reproductive Health Care, 1999, (Suppl. 2): 9-15.

* cited by examiner

*Primary Examiner* — San-Ming Hui
(74) *Attorney, Agent, or Firm* — Jason D. Voight

(57)   ABSTRACT

The present invention relates to a hormonal contraceptive including 21 to 25 hormone-containing daily units, which contain a combination of ethinyloestradiol in an amount of ≥25 μg and chlormadinone acetate in an amount of ≥5 mg, and optionally 7 to 3 hormone-free daily units for oral administration to women.

16 Claims, No Drawings

HORMONAL CONTRACEPTIVE CONTAINING A COMBINATION OF ETHINYLOESTRADIOL AND CHLORMADINONE ACETATE

CROSS-REFERENCE OF RELATED APPLICATIONS

This application claims priority from German Patent Application No. 10 2004 026 670.0 filed on May 28, 2004.

BACKGROUND OF THE INVENTION

1. Field of the Invention

The present invention relates to a hormonal contraceptive consisting of 21 to 25 hormone-containing daily units containing a combination of ethinyloestradiol in amount less than or equal to 25 µg and chlormadinone acetate in amounts of less than or equal to 5 mg, and optionally 7 to 3 daily units for oral administration to women.

In contraceptives, a combination of an oestrogen and a gestagen is conventionally administered per daily unit, wherein the amount of oestrogen should be kept as low as possible.

For all women, but in particular for women over 35 and in particular for women in the pre- and perimenopause, a hormonal contraceptive with the lowest possible amount of oestrogen is desirable, since from the age of 35 women have a greater risk of suffering complications caused by oestrogen-containing contraceptives, such as heart attack, stroke and lower limb thrombosis, followed by pulmonary embolisms.

2. Brief Description of Related Developments

It is already known from the prior art to use a combination of 30 µg of ethinyloestradiol and 2 mg of chlormadinone acetate for contraception and optionally for simultaneous treatment of acne. There is additionally a need to reduce still further the amount of ethinyloestradiol, which is combined with chlormadinone acetate, provided that reliable contraceptive action is nevertheless still guaranteed.

Furthermore, the contraceptive action of combined preparations of 15 µg of ethinyloestradiol and 60 µg of gestodene, which are administered for 24 days per cycle, is already known (Sullivan et al, Fertility and Sterility 72 (1999) 115-120; Gestodene Study Group 322, The European Journal of Contraception and Reproductive Health Care 4 (Suppl. 2) (1999) 9-15). However, gestodene does not ensure the advantageous properties of chlormadinone acetate.

Further combined preparations for hormonal contraception and for simultaneous treatment of complaints in the pre- and perimenopause are known from EP 0 398 460 and EP 0 253 607; these do not contain any chlormadinone acetate as the gestagen, however.

SUMMARY OF THE INVENTION

It was therefore the object of the present invention to provide a hormonal contraceptive containing chlormadinone acetate as the gestagen combined with a smaller amount of ethinyloestradiol compared with the prior art, but nonetheless guaranteeing a reliable contraceptive action.

This object is achieved by the hormonal contraceptive according to the invention, which consists of 21 to 25, preferably 21 to 24, hormone-containing daily units, which contains ethinyloestradiol in amounts of less than or equal to 25 µg, preferably of less than or equal to 20, and chlormadinone acetate in amount of less than or equal to 5 mg, preferable of less than or equal to 3 mg, and optionally 7 to 3, preferably 7 to 4, hormone-free daily units for oral administration to women.

The use of chlormadinone acetate ensures a high level of a contraceptive reliability and is distinguished by its pronounced antiandrogenic properties, which is suitable for all women of reproductive age since many women suffer androgen-dependent symptoms, such as acne, hirsutism (e.g. unwanted facial hair), androgenetic alopecia and seborrhoea. In addition, women with period problems (dysmenorrhoea) may be helped with the contraceptive according to the invention. The contraceptive according to the invention is also suitable in particular for contraception in women over 35, since it reduces the risk of thrombosis.

The hormonal contraceptive according to the invention comprises chlormadinone acetate in amount of less than or equal to 5 mg, preferable of 1 to 4 mg, very particularly preferably of 1 to 3 mg, and ethinyloestradiol in an amount of 25 µg, preferably of 10 to 20 µg, very particularly preferably of 15 to 20 µg.

Very particularly preferably, all the hormone-containing daily units of the contraceptive according to the invention each contain 2 mg of chlormadinone acetate and 20 µg of ethinyloestradiol and are taken by a woman as a monophasic contraceptive on 21 to 24 consecutive days of her cycle, followed by an interval in taking or the taking of hormone-free daily units for 7 to 4 days.

However, the contraceptive according to the invention may also take the form of a multiphasic contraceptive. In the case of a multiphasic contraceptive, a two-phase or a three-phase pill may be present.

The hormone-containing daily units of a multiphasic contraceptive according to the invention preferably comprise ethinyloestradiol in an amount of 20 µg and chlormadinone acetate in an amount of 1 or 3 mg. In the case of a two-phase contraceptive, the cycle preferably starts with taking daily a daily unit containing 1 to 2 mg of chlormadinone acetate in addition to EE for 7-12 days and ends with taking daily a daily unit of 2 to 3 mg of chlormadinone acetate for 9-18 days. In the case of a three-phase contraceptive, the tablet-taking cycle preferably starts with taking chlormadinone acetate daily in an amount of 1 to 2 mg for 6-7 days followed by taking chlormadinone acetate daily in an amount of 2 mg for 5-9 days and ends with taking chlormadinone acetate daily in an amount of 2 to 3 mg for 5-14 days.

The hormonal daily units each contain 20 µg of ethinyloestradiol.

In addition, to achieve maximum reliability of contraceptive action, it is particularly important to continue taking the hormone-containing daily units for 21 to 25 consecutive days per cycle.

In a tablet-taking cycle, there may be an interval in taking of 7 to 3 days or 7 to 3 hormone-free daily units may be taken daily before or after a tablet-taking phase of 21 to 25 hormone-containing daily units.

The daily units of the hormonal contraceptive according to the invention may preferably assume the form of tablets. Production methods for such daily units are known to the person skilled in the art. Known auxiliary substances may be used as additives in addition to the combination of chlormadinone acetate and ethinyloestradiol.

EXAMPLES

Example 1

| a) Composition | |
|---|---|
| | Per tablet |
| Ethinyloestradiol | 0.020 mg |
| Chlormadinone acetate | 2.000 mg |
| Povidone K30 | 3.000 mg |
| Lactose | 31.980 mg |
| Maize starch | 12.000 mg |
| Magnesium stearate | 0.500 mg |
| Highly disperse silicon dioxide | 0.500 mg |

Ethinyloestradiol (EE) and povidone K30 (polyvinylpyrrolidone) were dissolved in 600 ml of ethanol. Chlormadinone acetate (particle size 90%<50 μm), lactose and maize starch were mixed in a mixer/pelletiser (Diosna P25) for 5 mins and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg.

b) As indicated under a), hormone-free, folic acid-containing tablets with a weight of 50 mg were produced, wherein the sodium salt of the folic acid was dissolved in 600 ml of aqueous ethanol.

| | Per tablet |
|---|---|
| Sodium folate | 3.000 mg |
| Povidone K30 | 3.000 mg |
| Lactose | 31.000 mg |
| Maize starch | 12.000 mg |
| Magnesium stearate | 0.500 mg |
| Highly disperse silicon dioxide | 0.500 mg |

The tablets were coated with a methylhydroxypropylcellulose-based coating (e.g. Opadry YS-1-2184 made by Colorcon), coating composition 2 mg per tablet, and packaged into a dosage form comprising 120 hormone-containing daily units without folic acid and 7 hormone-free daily units with folic acid.

The invention claimed is:

1. A hormonal contraceptive for oral administration to a woman, comprising 21 to 25 hormone-containing daily units, each of said daily units comprising a combination of ethinyloestradiol in an amount of less than or equal to 20 μg and chlormadinone acetate in an amount of less than or equal to 3 mg, and optionally 7 to 3 hormone-free daily units,
   wherein the woman is over 35 years of age, and
   wherein the woman is in pre- or perimenopause.

2. A hormonal contraceptive according to claim 1, wherein the hormone-containing daily units each comprises 10 to 20 μg of ethinyloestradiol and 1 to 3 mg of chlormadinone acetate.

3. A hormonal contraceptive according to claim 1, wherein the hormone-containing daily units each comprises 20 μg of ethinyloestradiol and 2 mg of chlormadinone acetate.

4. A hormonal contraceptive according to claim 1, wherein the hormone-containing daily units and the optionally present hormone-free daily units are in the form of tablets.

5. A hormonal contraceptive according to claim 1, wherein each of the hormone-containing daily units comprises the same amount of ethinyloestradiol.

6. A method for producing a contraceptive effect in a woman comprising administering to said woman a hormone-containing daily unit on 21 to 25 consecutive days, followed by an interval in said administering of 7 to 3 days or by administering to said woman hormone-free daily units on 7 to 3 consecutive days, wherein each hormone-containing daily unit comprises a combination of ethinyloestradiol in an amount of less than or equal to 20 μg and chlormadinone acetate in an amount of less than or equal to 3 mg,
   wherein the woman is over 35 years of age, and
   wherein the woman is in pre- or perimenopause.

7. The method according to claim 6, wherein the hormone-containing daily units are administered on 21 to 24 consecutive days, followed by an interval in said administering of 7 to 4 days or by administering to said woman of hormone-free daily units on 7 to 4 consecutive days.

8. A hormonal contraceptive according to claim 1, wherein the hormone-containing daily units each comprises 2 mg of chlormadinone acetate.

9. The method according to claim 6 wherein the woman is in perimenopause.

10. The method of claim 6, wherein each hormone-containing daily unit comprises 10 to 20 μg of ethinyloestradiol and 1 to 3 mg of chlormadinone acetate.

11. The method of claim 6, wherein the hormone-containing daily units each comprises 20 μg of ethinyloestradiol and 2 mg of chlormadinone acetate.

12. The method of claim 6, wherein the hormone-containing daily units and the optionally present hormone-free daily units are in the form of tablets.

13. The method of claim 6, wherein each of the hormone-containing daily units comprises the same amount of ethinyloestradiol.

14. A hormonal contraceptive according to claim 1, wherein the hormone-containing daily units each comprises 15 to 20 μg of ethinyloestradiol.

15. The method of claim 6, wherein each hormone-containing daily unit comprises 15 to 20 μg of ethinyloestradiol.

16. The method of claim 6 wherein the hormone-containing daily unit administered on the first 7 to 12 of said 21 to 25 consecutive days comprises a combination of ethinyloestradiol in an amount of 20 μg and chlormadinone acetate in an amount of 1 to 2 mg, and the hormone-containing daily unit administered on the remaining 9 to 18 of said 21 to 25 consecutive days comprises a combination of ethinyloestradiol in an amount of 20 μg and chlormadinone acetate in an amount of 2 to 3 mg.

* * * * *